United States Patent
Boogers et al.

(10) Patent No.: US 6,803,460 B2
(45) Date of Patent: Oct. 12, 2004

(54) PROCESS FOR THE FERMENTATIVE PRODUCTION OF CEPHALOSPORIN

(75) Inventors: Ilco Adrainus Lambertus Antonius Boogers, Naaldwijk (NL); Emilius Johannes Albertus Xaverius Van De Sandt, Rotterdam (NL); Dick Schipper, Delft (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/254,622

(22) Filed: Sep. 24, 2002

(65) Prior Publication Data

US 2003/0139595 A1 Jul. 24, 2003

Related U.S. Application Data

(63) Continuation of application No. 09/647,056, filed as application No. PCT/EP99/02247 on Mar. 27, 1999, now Pat. No. 6,552,185.

(30) Foreign Application Priority Data

Mar. 27, 1998 (EP) ............................................. 98201011

(51) Int. Cl.[7] .................... C07D 501/12; C07D 463/20; C07D 505/20
(52) U.S. Cl. ........................ 540/205; 540/301; 540/220
(58) Field of Search ................................. 540/205, 301, 540/220; 435/51, 119

(56) References Cited

U.S. PATENT DOCUMENTS

| | | | |
|---|---|---|---|
| 3,658,649 A | 4/1972 | Arnold | 540/228 |
| 4,189,574 A | 2/1980 | Barthelemy | 540/228 |
| 5,559,005 A | 9/1996 | Conder et al. | 435/183 |
| 6,319,684 B1 | 11/2001 | Krijgsman et al. | 437/147 |
| 6,552,185 B1 * | 4/2003 | Boogers | 540/220 |

FOREIGN PATENT DOCUMENTS

| | | |
|---|---|---|
| EP | 0532341 | 3/1993 |
| EP | 0540210 | 5/1993 |
| WO | WO 93/08287 | 4/1993 |
| WO | WO 95/04148 | 2/1995 |
| WO | WO 98/48036 | 10/1998 |

OTHER PUBLICATIONS

Matsumoto K. (1993). *Bioprocess Techn* 16:67–68.
Shewale J. and Sivaraman H. (1989). *Process Biochemistry* 146–154.
Shewale J. et al. (1990). *Process Biochemistry International* 97–103.

* cited by examiner

*Primary Examiner*—Mark L. Berch
(74) *Attorney, Agent, or Firm*—Morrison & Foerster LLP

(57) ABSTRACT

A method for the recovery of an N-substituted cephalosporanic acid compound of general formula (I), wherein $R_2$ is selected from the group consisting of adipyl (1,4-dicarboxybutane), succinyl, glutaryl, adipyl, pimelyl, suberyl, 2-carboxyethyithio)acetyl, 3-carboxyethylthio) propionyl, higher alkyl saturated and higher alkyl unsaturated dicarboxylic acids, from a complex mixture comprising in addition to the compound of general formula (I) 6-aminopenicillanic acid (6-APA) and optionally one or more N-substituted penicillanic acid compounds, comprising the steps of: (a) acidifying the complex mixture to a pH below 6.5 and maintaining the mixture below said pH at a temperature of between 10° C. and 150° C.; and/or (b) contacting the complex mixture with a carbon dioxide source; and (c) recovering the cephalosporanic acid compound of formula (I) from the mixture obtained after steps (a) and/or (b).

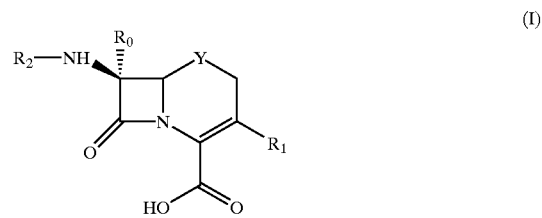

(I)

17 Claims, No Drawings

PROCESS FOR THE FERMENTATIVE PRODUCTION OF CEPHALOSPORIN

This application is a continuation of U.S. Ser. No. 09/647,056 filed Nov. 16, 2000, now U.S. Pat. No. 6,552,185, which is the national phase of PCT application PCT/EP 99/02247 filed Mar. 27, 1999 which claims priority to European application 98/201011.8 filed 27 Mar. 1998.

FIELD OF THE INVENTION

The present invention relates to a process for the preparation of cephalosporins and cephalosporin derivatives. More in particular, the present invention relates to the recovery of cephalosporins and derivatives thereof from complex mixtures of cephalosporins and other beta-lactam compounds. The invention is also concerned with recovery of deacylated cephalosporins from mixtures of beta-lactam compounds and side chains, such as those obtainable by enzymatic side-chain removal.

BACKGROUND OF THE INVENTION

Semi-synthetic routes to prepare cephalosporins mostly start from fermentation products such as penicillin G, penicillin V and Cephalosporin C, which are converted to the corresponding β-lactam nuclei, for instance in a manner as is disclosed in K. Matsumoto, Bioprocess. Techn., 16, (1993), 67–88, J. G. Shewale & H. Sivaraman, Process Biochemistry, August 1989, 146–154, T. A. Savidge, Biotechnology of Industrial Antibiotics (Ed. E. J. Vandamme) Marcel Dekker, New York, 1984, or J. G. Shewale et al., Process Biochemistry International, June 1990, 97–103. The obtained β-lactam nuclei are subsequently converted to the desired antibiotic by coupling to a suitable side chain, as has been described in inter alia EP 0 339 751, JP-A-53005185 and CH-A-640 240. By making different combinations of side chains and β-lactam nuclei, a variety of penicillin and cephalosporin antibiotics may be obtained.

7-Amino desacetoxy cephalosporanic acid (7-ADCA) and 7-aminocephalosporonic acid (7-ACA) are known to be the most important intermediates for the production of antibiotics used in the pharmaceutical industry.

7-ADCA is for example obtained by chemical or enzymatic cleavage (deacylation) of phenylacetyldesacetoxy cephalosporanic acid yielding 7-amino desacetoxy cephalosporanic acid and phenyl acetic acid.

Phenylacetyldesacetoxy cephalosporanic acid is normally produced by chemical treatment of penicillin G sulfoxide, which is formed from penicillin G. In this production process a large amount of chemicals are required to ensure that the desired reaction take place. This is both expensive and places a heavy burden on waste management. Moreover, the total yield of the process, is not very high.

To overcome some of the drawbacks of the chemical process a fermentative process has been disclosed for the production of 7-ADCA, 7-amino desacetyl cephalosporanic acid (7-ADAC) and 7-ACA, involving fermentative production of N-substituted β-lactams, such as adipyl-7-ADCA, adipyl-7-ADAC or adipyl-7-ACA by a recombinant *Penicillium chrysogenum* strain capable of expressing a desacetoxycephalosporanic acid synthetase (DAOCS) also known as "expandase" from a transgene (EP 0 532 341, EP 0 540 210, WO 93/08287, WO 95/04148). The expandase takes care of the expansion of the 5-membered ring of certain N-acylated penicillanic acids, thereby yielding the corresponding N-acylated desacetoxycephalosporanic acids.

In order to yield the economically most important non-acylated cephalosporins, such as 7-ADCA, 7-ADAC and 7-ACA, the acyl groups are enzymatically removed with a suitable acylase.

Known processes for recovering chemically or enzymatically produced penicillanic and cephalosporanic acids are not effective for the recovery of the N-substituted β-lactam intermediates and deacylated amino-β-lactams. The main problem with the recovery of the fermentatively produced cephalosporin compounds mentioned above is the complexity of the broth, or culture filtrate. The broth usually comprises various penicillanic acids, such as alpha-aminoadipyl-6-penicillanic acid, alpha-hydroxyadipyl-6-penicillanic acid, 6-aminopenicillanic acid (6-APA), various cephalosporanic acids including alpha-aminoadipyl- and hydroxyadipyl-7-ADCA and a lot of proteinaceous material. Known recovery procedures do not give an acceptable quality of the cephalosporanic acid product in terms of purity. In deacylation this leads to problems in terms of reduced enzyme half-life, slower bioconversion rate and more expenses in the recovery after bioconversion and/or unacceptable contaminant levels. Moreover, after deacylation, such impurities prevent or at least hamper the recovery of the desired deacylated cephalosporin compound of the desired specifications.

SUMMARY OF THE INVENTION

The invention provides for a method for the recovery of a cephalosporanic acid compound of the general formula (I):

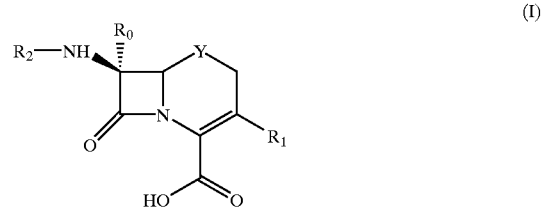

wherein
$R_0$ is hydrogen or $C_{1-3}$ alkoxy;
Y is $CH_2$, oxygen, sulphur, or an oxidised form of sulphur;
$R_1$ is any of the groups selected from the group consisting of
hydrogen,
hydroxy,
halogen,
saturated or unsaturated, straight or branched alkyl (1–5 carbon atoms; optionally replaced by one or more heteroatoms), optionally substituted with hydroxy, halogen, aryl, alkoxy (1–3 carbon atoms), or acyl;
alkoxy (1–3 carbon atoms; optionally replaced by one or more heteroatoms), optionally substituted with hydroxy or halogen; or
cycloalkyl (3–8 carbon atoms) optionally substituted with hydroxy, halogen, amino;
aryl;
heteroaryl; and
$R_2$ is selected from the group consisting of adipyl (1,4-dicarboxybutane), succinyl, glutaryl, adipyl, pimelyl, suberyl, 2-(carboxyethylthio)acetyl, 3-(carboxyethylthio)propionyl, higher alkyl saturated and higher alkyl unsaturated dicarboxylic acids,
from a complex mixture comprising in addition to the compound of the general formula 6-aminopenicillanic acid (6-APA) and optionally one or more N-substituted β-lactam compounds, comprising the steps of:
(a) acidifying the complex mixture to a pH below 6.5 and maintaining the mixture below said pH at a temperature of between 10° C. and 150° C.; and/or
(b) contacting the complex mixture with a carbon dioxide source; and
(c) recovering the cephalosporanic acid compound of the formula (I) from the mixture obtained after steps (a) and/or (b).

Preferably in step (a) the temperature is kept between about 50° C. and about 130° C., preferably between 70 and 120° C., for between 10 seconds and about 1 week and the pH is kept at or below pH 4.5. According to a preferred method the compound of formula (I) has been produced by fermentation of a micro-organism capable thereof, the complex mixture being a broth, a culture filtrate or any culture liquid derivable from the broth after fermentation.

Preferred compounds of the general formula (I) are selected from the group consisting of adipyl-7-ADCA, adipyl-7-ADAC and adipyl-7-ACA.

According to another aspect of the invention step (c) is performed by subjecting the mixture obtained after steps (a) and/or (b) to chromatography, preferably adsorption chromatography, more preferably Hydrophobic Interaction Chromatography.

According to another aspect of the invention the use of chromatography in a process of recovering a cephalosporin compound according to formula (I) is provided, preferably by adsorption chromatography, more preferably Hydrophobic Interaction Chromatography, still more preferably using Simulated Moving Bed technology.

According to yet another aspect of the invention a method is provided for making a compound of formula (II):

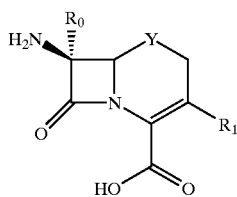

(II)

wherein
$R_0$ is hydrogen or $C_{1-3}$ alkoxy;
Y is $CH_2$, oxygen, sulphur, or an oxidised form of sulphur;
$R_1$ is any of the groups selected from the group consisting of
hydrogen,
hydroxy,
halogen,
saturated or unsaturated, straight or branched alkyl (1–5 carbon atoms; optionally replaced by one or more heteroatoms), optionally substituted with hydroxy, halogen, aryl, alkoxy (1–3 carbon atoms), or acyl;
alkoxy (1–3 carbon atoms; optionally replaced by one or more heteroatoms), optionally substituted with hydroxy or halogen; or
cycloalkyl (3–8 carbon atoms) optionally substituted with hydroxy, halogen, amino;
aryl;
heteroaryl;
comprising the steps of making a compound according to formula (I) wherein $R_0$, Y and $R_1$ are as above and $R_2$ is selected from the group consisting of adipyl (1,4-dicarboxybutane), succinyl, glutaryl, adipyl, pimelyl, suberyl, 2-(carboxyethylthio)acetyl, 3-(carboxyethylthio)-propionyl, higher alkyl saturated and higher alkyl unsaturated dicarboxylic acids;
deacylating the compound of formula (I) to obtain a conversion solution which comprises a compound according to formula (II).

The conversion solution preferably further comprises the cleaved side chain designated $R_2$.

According to a preferred embodiment, the process comprises the further step of recovering the compound of formula (II) from the solution by crystallisation, preferably preceded and/or followed (after solubilisation of the crude crystals i.e. by crystallisation) by treatment of the solution with an agent selected such as activated carbon or an adsorber resin. According to another aspect of the invention during or before crystallisation and/or recrystallisation a solvent such as methanol, ethanol, (iso)propanol, isobutanol, n-butanol, or acetone or a combination of any of the mentioned agents is added. Preferred adsorber resins are selected from XAD16 (CAS No. 102419-63-8), XAD1600 (CAS No. 153796-66-8) and HP20 (CAS No. 55353-13-4). Preferred according to the invention is a method wherein the 6-aminopenicillanic acid (6-APA) level is 10 ppm or less with respect to the compound of formula (II). According to another aspect, a process is provided wherein following the deacylation the solution is treated to remove, at least partially, the cleaved side chain represented by $R_2$. This step may be performed, or repeated, after crystallisation and solubilisation (i.e. recrystallisation) of the compound of formula (II). Also removal of the cleaved side-chain may be carried out on the mother liquor obtained after crystallisation or recrystallisation.

Thus, a process is provided wherein said treatment to remove, at least partially, the cleaved side chain is followed by solubilisation of the crude crystals and recrystallisation of the compound of formula (II).

Preferably said treatment to remove the cleaved side chain comprises subjecting the conversion solution, or the mother liquor, or both, to membrane filtration at a pH below 5, preferably below 4, more preferably near or below 3. Accordingly, the use is provided of membrane filtration to remove a dicarboxylic acid from a mixture comprising the dicarboxylic acid and a β-lactam antibiotic. The mixture is preferably a mother liquid obtained after crystallisation of a compound of the formula (II) or the mixture obtained after deacylation of the compound of formula (I). Membrane filtration takes preferably place at a pH of about 5 or less, preferably at pH 4 or less, yet more preferably by nanofiltration at or below pH 3.

According to another aspect of the invention, a process is provided wherein the side chain $R_2$ is, at least partially, removed from the conversion mixture by crystallisation and/or recrystallisation.

According to still another aspect of the invention, a process is provided wherein the side chain $R_2$ is, at least partially, removed from the conversion mixture by acidifying the mixture to a pH lower than 3 and next contacting this mixture with an organic solvent, for instance amyl acetate, butyl acetate, ethyl acetate, methyl isobutyl ketone, cyclohexanone, isobutanol or n-butanol.

DETAILED DESCRIPTION OF THE INVENTION

The invention pertains to a method for the recovery of a cephalosporanic acid compound of the general formula (I):

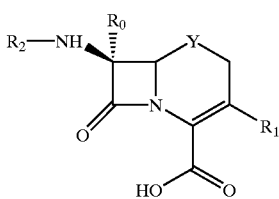

(I)

wherein $R_0$ is hydrogen or $C_{1-3}$ alkoxy;

Y is $CH_2$, oxygen, sulphur, or an oxidised form of sulphur;

$R_1$ is any of the groups selected from the group consisting of hydrogen, hydroxy, halogen, saturated or unsaturated, straight or branched alkyl (1–5 carbon atoms; optionally replaced by one or more heteroatoms), optionally substituted with hydroxy, halogen, aryl, alkoxy (1–3 carbon atoms), or acyl;

alkoxy (1–3 carbon atoms; optionally replaced by one or more heteroatoms), optionally substituted with hydroxy or halogen; or cycloalkyl (3–8 carbon atoms) optionally substituted with hydroxy, halogen, amino;

aryl;

heteroaryl; and $R_2$ is selected from the group consisting of adipyl (1,4-dicarboxybutane), succinyl, glutaryl, adipyl, pimelyl, suberyl, 2-(carboxyethylthio)acetyl, 3-(carboxyethylthio)propionyl, higher alkyl saturated and higher alkyl unsaturated dicarboxylic acids, from a complex mixture comprising in addition to the compound of the general formula 6-aminopenicillanic acid (6-APA) and optionally one or more N-substituted penicillanic acid compounds, comprising the steps of:

(a) acidifying the complex mixture to a pH below 6.5 and maintaining the mixture below said pH at a temperature of between 10° C. and 150° C.; and/or (b) contacting the complex mixture with a carbon dioxide source; and (c) recovering the cephalosporanic acid compound of the formula from the mixture obtained after steps (a) and/or (b). The invention relates further to a process for the preparation of cephalosporins having the general formula (II):

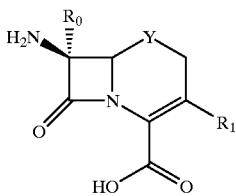

(II)

wherein $R_0$ is hydrogen or $C_{1-3}$ alkoxy;

Y is $CH_2$, oxygen, sulphur, or an oxidised form of sulphur;

$R_1$ is any of the groups selected from the group consisting of hydrogen, hydroxy, halogen, saturated or unsaturated, straight or branched alkyl (1–5 carbon atoms; optionally replaced by one or more heteroatoms), optionally substituted with hydroxy, halogen, aryl, alkoxy (1–3 carbon atoms), or acyl;

alkoxy (1–3 carbon atoms; optionally replaced by one or more heteroatoms), optionally substituted with hydroxy or halogen; or cycloalkyl (3–8 carbon atoms) optionally substituted with hydroxy, halogen, amino;

aryl;

heteroaryl.

The compound according to formula (I) may be produced by any series of steps which yield a complex mixture as defined herein, from which the recovery of the compound according to formula (I) is accomplished. For the purposes of the specification and claims, a complex mixture is defined as a mixture comprising a N-substituted cephalosporin compound and substituted or unsubstituted β-lactam compounds.

The compound of formula (II) is obtained by the following series of steps:

(a) recovering, preferably purifying, the compound of formula (I);

(b) deacylating the preferably purified compound of formula (I) to obtain a solution comprising the compound of formula (II) (the conversion solution); and (c) recovering, preferably purifying the compound of formula (II).

One of the obstacles of producing N-substituted cephalosporanic acid fermentatively is the presence of unwanted contaminating β-lactam components, for instance N-substituted 6-amino penicillanic acid. According to one embodiment of the invention, it has been found that these contaminations can be remarkably reduced by incubating the broth, the filtrate of the broth or a liquid derived from the broth using any biomass separation technique, under acidified conditions, preferably accompanied with an elevated temperature. The broth is acidified down to a pH lower than 6.5, preferable lower than 4.5, using at least one known acid, for instance sulphuric acid, hydrochloric acid or nitric acid or a combination thereof. Operating temperature is in the range of 20 to 150° C., preferably at 70 to 120° C. Residence time at these conditions is in the range of a few seconds (at 150° C.), or several days (at 20° C.), preferably 10 seconds to 60 minutes. The pH/temperature treatment is preferably carried out for a period which provides for an N-substituted 6-APA reduction of a factor 100, preferably 1000, more preferably 1,000,000 with respect to the compound of formula (II). This step can be carried out either before or after biomass separation and can be performed batch wise or continuously.

According to another embodiment of the invention contaminating penicillin components, for instance N-substituted 6-APA, are remarkably reduced by contacting the broth, the filtrate of the broth, the eluate, the conversion solution or the dissolved contaminated cephalosporin according to formula (I), typically at pH 5 to 7, with carbon dioxide. Carbon dioxide can be added to the solution in any suitable way, such as solid or gaseous form or as solution of carbonate ions. The solution is contacted with the $CO_2$ source at a temperature of 10 to 60° C., preferably 20 to 40° C., where said solution is saturated with molecular $CO_2$ for 4 to 10 hours. After reduction of the penicillin components, purification of the cephalosporins, according to formula 1 can be obtained as mentioned earlier.

The complex mixture as defined herein may have any origin, but is preferably a culture broth or a culture filtrate obtained after fermenting under conditions giving rise to production, a micro-organism capable of producing an 7-N-acylated version of the compound of the general formula (I), wherein the acyl-group may be any acyl-group which supports the ring-expanding enzyme (desacetoxycephalosporin synthetase—DAOCS—or a bifunctional expandase/ hydroxylase occasionally referred to as desacetylcephalosporin synthetase DACS) in the cephalosporin biosynthetic pathway. Bioprocesses for producing 7-N acyl-substituted compounds according to formula (I) in vivo are disclosed in WO 93/05158 (adipyl-7-ADCA); WO 93/08287 (adipyl-7-ADAC and adipyl-7-ACA), WO 95/04148 (2-(carboxyethylthio)acetyl-7-ADCA), WO 95/04149 (3-(carboxyethylthio)propionyl-7-ADCA) and higher alkyl saturated or unsaturated dicarboxylic acids. The relevant parts of these PCT-applications are herein incorporated by reference. Preferred acyl grouts are dicarboxylic acid groups in general, such as adipyl (1,4-dicarboxybutane), 2-(carboxyethylthio)acetyl, 3-(carboxyethylthio)propionyl, muconic acid and the like. Suitable host organisms include but are not limited to *Penicillium chrysogenum* and *Acremonium chrysogenum*. Suitable sources of expandases, including bifunctional expandase/hydroxylases include but are not limited to *Streptomyces clavuligerus* and *Acremonium chrysogenum*. Methods for transformation, selection of transformed cells and expression regulating elements for filamentous fungi, which may be used to genetically modify host cells, are well known in the art of recombinant DNA technology of β-lactam producing (filamentous) fungi.

Preferably, the broth is subjected first to biomass separation such as filtration by any suitable means, such as membrane filtration, vacuum filtration, ultrafiltration or a combination thereof, prior to acidification and the optional temperature increase. Any other means of biomass separation is suitable as well.

After the pH-lowering step and the optional temperature step, the recovered compound according to the formula (I) is preferably subjected to further purification to remove, at least partially, unwanted β-lactam components, especially unwanted N-substituted cephalosporins and penicillins. The further purification may be carried out by extraction using an organic solvent. In the case of extraction, it is found to be advantageous to wash the extract, back extract the N-substituted cephalosporin from the organic phase to an aqueous phase and stripping the aqueous phase. The extracting organic solvent may be selected from amyl acetate, butyl acetate, ethyl acetate, methyl isobutyl ketone, cyclohexanone, iso-butanol or n-butanol, and the like. A preferred purification step in the process is the usage of chromatography for the purification of N-substituted cephalosporin, rather than extraction using organic solvents. The advantage of chromatography is in the absence of solvents, which cause waste problems and problems of containment, as well as improved purity of the final product. Preferred is ion exchange chromatography or adsorption chromatography, more preferably Hydrophobic Interaction Chromatography. The filtrate is subjected to chromatography using an adsorbent. An adsorbent includes activated carbon, e.g. Norit CG-1 or Cecarbon GAC 40; or an adsorber resin, such as styrene-divinylbenzene copolymerisates, for example Dianion HP 20 (CAS No. 55353-13-4), Dianion HP 21 (CAS No. 92529-04-9), Dianion SP 207 (CAS No. 98225-81-1) or Dianion SP825, from Mitsubishi Kasei Corporation or Amberlite XAD 1180 (CAS No. 97396-56-0), Amberlite XAD 1600 (CAS No. 153796-66-8) or Amberlite XAD 16 (CAS No. 102419-63-8) from Rohm and Haas or Amberchrom CG 161 (CAS No. 131688-63-6) from TosoHaas; preferably XAD 16 or XAD 1600.

Before adsorbing the N-substituted cephalosporin the complex mixture is adjusted to a pH of 1.0 to 5.0, preferably 2.5 to 3.5, by the means of one or more known acids, for instance sulphuric acid, hydrochloric acid or nitric acid or a combination thereof. Operating temperature is the range of 0 to 50° C., preferably at 5 to 25° C. Operating pressure is in the range of 0 to 1.0 MPa overpressure.

Unwanted β-lactam components, especially unwanted N-substituted cephalosporins, such as alpha-aminoadipylcephalosporanic acids, also adsorb on the adsorbent but are displaced by the wanted N-substituted cephalosporin.

After adsorbing, washing with water is applied to remove unwanted β-lactam components from the void volume between the adsorbent and to desorb weakly bound unwanted β-lactam components from the adsorbent. The water can be acidified down to a pH of 1.0 by the means of one or more known acids, for instance sulphuric acid, hydrochloric acid or nitric acid or a combination thereof. To increase the osmotic pressure, salts may be added to the water. Operating temperature is the range of 0 to 50° C., preferably at 20 to 40° C. Operating pressure is in the range of 0 to 1.0 MPa overpressure.

Elution may be carried out with a suitable buffer, such as acetate, phosphate, carbonate, bicarbonate or adipate but also diluted organic solvents (e.g. acetone, isopropanol) or diluted bases (e.g. ammonium, caustic) can be used. Operating temperature is the range of 0 to 80° C., preferably at 10 to 40° C. Operating pressure is in the range of 0 to 1.0 MPa overpressure.

Regeneration of the adsorbent can be done by any common applied method, such as with dilute bases, dilute acids, or with water miscible solvents (such as acetone, methanol, ethanol or iso-propanol), or a combination thereof. Optionally heating up to 100° C. may be performed.

The regeneration liquids can be removed by washing with water. The water can be acidified down to a pH of 1.0 by the means of one or more known acids, for instance sulphuric acid, hydrochloric acid or nitric acid or a combination thereof.

The chromatography step can be performed in several types of equipment, such as in a single column but also the simulated moving bed technology can be applied. For this simulated moving bed technology several types of equipment are available, such as the ADSEP system from U.S. Filter, the ISEP/CSEP-system from Advanced Separation Technology, the 'merry-go-around'-system from e.g. Applexion or the SORBEX-system from Universal Oil Products Company (UOP).

Alternatively, the buffer can be removed from the eluate by means of nanofiltration. The characteristics of the membrane in this membrane filtration show a high retention for the wanted N-substituted cephalosporin and a low retention for the buffer.

Optionally a concentration step is applied by any means of suitable concentration such as vacuum evaporation, reversed osmosis, nanofiltration, or narofiltration after chromatography or extraction.

The recovered N-acylated compound is subsequently subjected to deacylation using any suitable method known in the art. A preferred method is enzymatic deacylation using a suitable dicarboxylate acylase. Numerous suitable acylases, wild-type or mutated, are known in the art including but not limited to those from Bacillus (EP 0 525 861; EP 0 405 846) Pseudomonas (EP 0 482 844; EP 0 525 861; EP 0 475 652; EP 0663 445), Achromobacter (EP 0 525 861), *Alcaligenes faecalis* (EP 0 638 649), Acinetobacter (EP 0 469 919), Arthrobacter (EP 0 283 218), *Escherichia coli* (U.S. Pat. No. 3,945,888), *Kluyvera citrophila, Proteus rettgeri* (U.S. Pat. No. 3,915,798) and the like. The dicarboxylate acylase is preferably from Pseudomonas SE83 or SY-77. Optionally, the acylase may be a mutated form, as disclosed in WO 91/16435, WO 97/20053, WO 97/40175 to increase or alter the affinity towards the substrate. Another way of deacylating the N-acylated cephalosporin compound according to the invention is by way of contacting the substrate with a micro-organism capable of producing the acylase, as disclosed in U.S. Pat. No. 5,677,141.

The acylase may be immobilised (U.S. Pat. No. 3,930, 949), either on membranes (EP 0 243 404) or free flowing carriers such as glutaraldehyde based carriers or aza-lacton polymers (EP 0 730 035), using techniques as such well known in the art. Non-immobilised acylase is also contemplated, using membranes to separate the reaction mixture (retentate) from the product (permeate), such as disclosed in U.S. Pat. No. 5,521,068. The process may be batch-wise or (semi-)continuous, this is all well known and not crucial with respect to the invention. The enzymatic deacylation reaction is usually carried out in a stirred tank reactor with or without, preferably inert, sieve plates, to easily separate the immobilised enzyme from the reaction product. The pH is usually regulated during the reaction to compensate for the pH change as a result of the (dicarboxylic) side-chain removal by any type of base such as ammonium, caustic, carbonate, bicarbonate. The pH can be regulated in the reactor and/or in a circulating loop over the reactor. Other parameters may also be regulated, such as temperature, deacylated product or side-chain concentration, and the like, taking account of the effect of such parameters on the reaction rate and/or the equilibrium.

Additional stabilising agents can be added before and/or during deacylation, such as sulphite ($S_2O_5^{2-}$, $HSO_3^-$, $SO_3^{2-}$), EDTA, dithiotreitol (DTT).

Usually, the deacylated cephalosporin compound of the general formula (I) is subsequently recovered using any suitable combination of steps. Optionally a concentration step can be applied by any means such as vacuum evaporation, reversed osmosis, nanofiltration, or narofiltration before crystallisation. Optionally a water miscible solvent can be added. Optionally, before crystallisation the solution can be purified by treating with activated carbon or an adsorber resin. Optionally, before crystallisation the side chain can be removed, characterised by acidifying the aqueous phase, extracting the side chain to an extracting organic solvent and separating the phases. The extracting organic solvent may be selected from amyl acetate, butyl acetate, ethyl acetate, methyl isobutyl ketone, cyclohexanone, iso-butanol, n-butanol, and the like.

The product can be crystallised from the resulting aqueous phase in several ways. The most preferred mode of operation is neutralising the aqueous solution and subsequently lowering the pH in 1 to 6 steps down to a pH 3 to 5 using one or more known acids such as $H_2SO_4$, HCl, $HNO_3$, or a combination thereof. This is preferably carried out in continuous mode using an interconnected set of 1 to 6 continuously operated crystallisers in series. Also batch crystallisation, semi-continuous crystallisation or concordance crystallisation can be applied. It is possible to perform the crystallisation directly in the same way as above, without the first neutralisation. According to one embodiment of this invention it has been found that a water miscible solvent, such as methanol, ethanol, iso-propanol, n-butanol, acetone and the like, can be added to improve the quality of the cephalosporin according to formula (II) Optionally, before crystallisation the solution can be treated by activated carbon or by an adsorbent resin in order to improve the quality of the compound according to formula (II).

It has been found that the quality of the cephalosporin according to formula (II) can be further improved by recrystallisation, optionally after treatment with adsorber resins, active coal and/or ethanol and/or acetate. This is characterised by dissolving the cephalosporin according to formula (II) at a pH in the range of 0.5 to 10.0, preferably between 7.5 to 8.5 and crystallisation of the product. The product can be crystallised in several ways. The most preferred mode of operation is lowering of the pH in 1 to 6 steps down to a pH 3 to 5 using one or more known acids, such as $H_2SO_4$, HCl, $HNO_3$, or a combination thereof. This can be carried out in continuous mode using an interconnected set of 1 to 6 continuously operated crystallisers in series. Also batch crystallisation, semi-continuous crystallisation or concordance crystallisation can be applied. According to one embodiment of this invention it has been found that a water miscible solvent, such as methanol, ethanol, (iso)propanol, acetone, iso-butanol and n-butanol, can be added to improve the quality of the cephalosporin according to formula (II).

It has been found further, that the quality of the cephalosporin according to formula (II) can be improved by treating the conversion solution and/or the solution of the dissolved cephalosporin according to formula (II) with an adsorbent. An adsorbent includes activated carbon, e.g. Norit Ultra SX; or an adsorber resin, such as styrene-divinylbenzene copolymerisates, for example Dianion HP 20 (CAS No. 55353-13-4), Dianion HP 21 (CAS No. 92529-04-9) or Dianion SP 207 (CAS No. 98225-81-1) from Mitsubishi Kasei Corporation or Amberlite XAD 1180 (CAS No. 97396-56-0), Amberlite XAD 1600 (CAS No. 153796-66-8) or Amberlite XAD 16 (CAS No. 102419-63-8) from Rohm and Haas or Amberchrom CG 161 (CAS No. 131688-63-6) from TosoHaas; preferably XAD 16, XAD 1600 or HP20.

The crystals are isolated by filtration or centrifugation and dried in a conventional continuous or batch dryer. The crystals can be milled by any type of mill, such as ball mill, jet mill and the like.

Optionally a water miscible solvent can be added during the crystallisation. After dissolving, the solution can be treated with activated carbon or an adsorber resin.

This procedure will gave a better overall yield and product quality than the currently known process, mentioned before.

According to another aspect of the invention, a method is provided for removing and recovering adipic acid from the conversion solution or mother liquid (the liquid obtained after crystallisation of the compound according to the formula (II)). It is found, that adipic acid can advantageously separated using membrane filtration at low pH, such as below pH 5, preferably below pH 4, more preferably below at or near pH 3. Preferred according to the invention is an embodiment wherein filtration is carried out by reversed osmosis.

In addition to saving raw materials, the advantage of doing so resides in the purity and/or yield upon crystallisation of the so-treated solution.

The invention is further illustrated by the following non-limiting examples.
Experimental A fermentation broth comprising adipyl-7-ADCA as a complex mixture, comprising inter alia 6-APA, adipyl-6-APA and alpha-amino-adipyl-7-cephalosporanic acid as undesired contaminants, is obtained by fermenting a *Penicillium chrysogenum* strain transformed with an expandase (desacetoxycephalosporin C synthetase) from *Streptomyces clavuligerus*, as described in International patent application WO 93/05158, published on Mar. 18, 1993.

The transformed Penicillium strain was cultured as described in Example 1 of WO 93/05158, incorporated by reference herein.

After 5 to 7 days of fermentation, the broth was taken for recovery experiments.

This complex mixture can also be simulated by making an aqueous mixture of 6-aminopenicillanic acid, adipyl-6-aminopenicillanic acid, alpha-aminoadipyl-6-aminopenicillanic acid, adipyl-7-aminodesacetoxycephalosporanic acid, and alpha-aminoadipyl-7-cephalosporanic acid.

EXAMPLE 1 pH/Heat-Treatment

This example shows the advantages of a pH-treatment, preferably a combined pH-plus increased temperature treatment, on the removal of unwanted β-lactam components, from complex mixtures.

Broth from a fermentation of *Penicillium chrysogenum* (see experimental), containing a complex mixture of adipyl-7-ADCA and penicillanic acid and cephalosporanic acid contaminants is filtrated. The concentrate is washed with process water until the total volume of the combined filtrates was approx. 2 times the initial broth volume.

The following experiments have been carried out:

A. Part of the filtrate is acidified to pH=3.5; heated up to 70° C. and after 30 minutes cooled to 40° C.;
B. Part of the permeate is acidified to pH=2.7; heated up to 110° C. and after 4 minutes cooled to 25° C.; or
C. Part of the permeate is acidified to pH=3.0 and not further treated.

The pre-treated solutions are then subjected to the following treatments to obtain a compound according to formula (II); 7-ADCA.
Adsorption Chromatography The three solutions (A to C) were subjected to filtration over a Seitz K100 filter, whereafter the solution was pumped at a pH of 3.0 over a column filled with 1.6 liter of XAD-1600 resin; next the resin was washed with 4.8 liter water, and eluted with 0.2 M bicarbonate-solution. The first eluate fraction (1.1 liter) is taken out and discarded. The second fraction (3.2 liter) is collected and analysed. The resin is purified by washing with caustic and acetone, and conditioned again with acidified water.
Concentrating The eluate was concentrated at 20 to 30° C. vacuum (5-10 mm Hg) till a concentration of 40 grams adipyl-7-ADCA per liter was obtained.
Enzymatic Deacylation Subsequently, the adipyl-7-ADCA is treated with acylase as follows. To 1 liter of eluate, 1 gram of sodium metabisulfite, 20 mM EDTA and 100 g immobilised acylase (comprising Pseudomonas SE83 dicarboxylate acylase) was added. At 30° C., the solution was stirred for two hours. The pH was held at 8.5 with 4 N sodium hydroxide. The immobilised acylase and the liquid were separated with a glass sintered filter.

Crystallisation of 7-ADCA

The 7-amino desacetoxy cephalosporanic acid (7-ADCA) was precipitated by lowering the pH to 3.6, under stirring, at a temperature of 30° C.; in 45 minutes the pH of the solution was lowered to 3.6 with 6 N sulphuric acid. After cooling to 20° C., the crystals were isolated on a glass sintered filter, washed with water and dried at 35° C.
Resolving 7-ADCA Crystals The 7-ADCA was dissolved with the aid of ammonia. To that end 15 grams of 7-ADCA was suspended in 255 ml water. The 7-ADCA was dissolved with the aid of 4 N ammonium hydroxide at a pH of 7.5–8.5. After filtration over a glass sintered filter, water was added to obtain 300 ml of solution.
Treatment with Adsorber Resin The solution was treated with adsorber resin. In 45 minutes the solution was pumped over 15 ml of XAD1600. Subsequently, 75 ml of water was pumped over the resin to obtain 375 ml of solution.
Recrystallisation The 7-ADCA was precipitated by lowering the pH to 3.6 under stirring, at a temperature of 30° C.; in 45 minutes the pH was lowered to 3.6 with 6 N sulphuric acid. After cooling to 20° C., the crystals were isolated on a glass sintered filter, washed with water and dried at 35° C.

The 7-ADCA so produced shows good results in terms of 6-APA reduction. (6-APA ratio is with respect to 7-ADCA)

TABLE 1a

Results of experiment 1A, 1B and 1C.

| Experiment | 6-amino penicillanic acid content (ppm) |
| --- | --- |
| 1A | <10 |
| 1B | <10 |
| 1C | 950 |

Clearly, the pH/Temperature treatment reduces the level of 6-aminopenicillanic acid contamination of the adipyl-7-ADCA preparation.

The relationship between pH, Temperature and Time of treatment was determined for a fixed reduction of 6-aminopenicillanic acid of $10^{-6}$ (Table 1b).

TABLE 1b

| 6-APA reduction | pH | Temp. (C.) | Time (s) | Time (min) | Time (h) |
| --- | --- | --- | --- | --- | --- |
| $10^{-6}$ | 3 | 25 | 35050 | 584 | 9.74 |
| $10^{-6}$ | 3 | 50 | 3057 | 50.9 | 0.85 |
| $10^{-6}$ | 3 | 75 | 378 | 6.3 | 0.11 |
| $10^{-6}$ | 3 | 100 | 62 | 1.0 | 0.02 |
| $10^{-6}$ | 4 | 25 | 148857 | 2481 | 41.35 |
| $10^{-6}$ | 4 | 50 | 12982 | 216.4 | 3.61 |
| $10^{-6}$ | 4 | 75 | 1607 | 26.8 | 0.45 |
| $10^{-6}$ | 4 | 100 | 263 | 4.4 | 0.07 |

EXAMPLE 2

Adsorption Chromatography

This example shows the effect of (a) the degree of loading of the column when adsorption chromatography is used (2A to 2D), (b) the effect of washing the column with different amounts of water prior to elution (2E to 2G), (c) the effect of the pH of the feed on the purification of adipyl-7-ADCA (2H to 2J). The embodiment where adsorption chromatography is carried out in a Simulated Moving bed mode is given as Experiment 2K.

The broth is pre-treated as described in Example 1A. The adipyl-7-amino-desacetoxy cephalosporanic acid was subsequently purified by adsorption chromatography by pumping the solution over a column filled with 1.6 liter of XAD-1600 resin, washed with different amounts of water (2A to 2D and 2H to 2K: 4.8 liter; 2E to 2F: see Table 2b), and eluted with 0.2 M bicarbonate-solution. The first eluate fraction (1.1 liter) is taken out and discarded. The second fraction (3.2 liter) is collected and analysed. The resin is purified by washing with caustic and acetone, and conditioned again with acidified water. Several changes in process conditions were applied (see table 2).

Reduction is calculated as: $(\text{comp-i}_{feed}/\text{comp-l}_{feed})/(\text{comp-i}_{eluate}/\text{comp-l}_{eluate})$.

TABLE 2a

Results of experiment 2

| | Feed | | | Eluate (g) | | | Reduction (−) | | |
|---|---|---|---|---|---|---|---|---|---|
| | comp 1 | comp 2 | comp 3 | comp 1 | comp 2 | comp 3 | | | comp 4 |
| Exp | (g) | (g) | (g) | (g) | (g) | (g) | comp 2 | comp 3 | (ppm) |
| 2A | 34 | 3.3 | 9.3 | 30 | 3.1 | 5.9 | 1 | 1 | |
| 2B | 80 | 5.9 | 18.5 | 70 | 0.5 | 0.09 | 10 | 173 | <6 |
| 2C | 127 | 10.5 | 32.8 | 76 | 0.3 | 0.07 | 24 | 301 | 19 |
| 2D | 255 | 18.2 | 59.4 | 67 | 0.1 | 0.03 | 38 | 501 | 30 | comp 1: adipyl-7-ADCA
comp 2: alpha-hydroxy adipyl-7-ADCA
comp 3: alpha-amino adipyl-7-ADCA
comp 4: 6-APA content relative to comp 1

These results clearly show the positive effect of overloading the column on the reduction of compounds 2 and 3 in the eluate.

TABLE 2b

Results of experiment 2

| | Feed | | | | Eluate | | | Reduction (−) | |
|---|---|---|---|---|---|---|---|---|---|
| | comp 1 | comp 2 | comp 3 | Wash | comp 1 | comp 2 | comp 3 | | |
| Exp | (g) | (g) | (g) | (l) | (g) | (g) | (g) | comp 2 | comp 3 |
| 2E | 85 | 6.6 | 14.0 | 1.6 | 81 | 2.1 | 1.2 | 3 | 11 |
| 2F | 74 | 6.4 | 12.6 | 4.8 | 71 | 1.1 | 0.13 | 6 | 94 |
| 2G | 75 | 5.8 | 13.0 | 7.3 | 68 | 0.5 | 0.1 | 12 | 122 | comp 1: adipyl-7-ADCA
comp 2: alpha-hydroxyadipyl-7-ADCA
comp 3: alpha-amino adipyl-7-ADCA The example 2b shows the positive effect of extended washing, prior to elution with sodium bicarbonate, on the reduction of undesired cephalosporin compounds.

TABLE 2c

| | Feed | | | | Eluate | | | Reduction (−) | |
|---|---|---|---|---|---|---|---|---|---|
| | comp 1 | comp 2 | comp 3 | pH | comp 1 | comp 2 | comp 3 | | |
| Exp | (g) | (g) | (g) | (−) | (g) | (g) | (g) | comp 2 | comp 3 |
| 2H | 79 | 8.4 | 22.2 | 2.5 | 83 | 0.6 | 0.09 | 15 | 248 |
| 2I | 80 | 5.9 | 18.5 | 2.9 | 70 | 0.5 | 0.09 | 10 | 183 |
| 2J | 83 | 8.2 | 21.7 | 3.5 | 62 | 0.5 | 0.14 | 12 | 118 | comp 1: adipyl-7-ADCA
comp 2: alpha-hydroxy adipyl-7-ADCA
comp 3: alpha-amino adipyl-7-ADCA The above example shows the effect of the pH at which crystallisation was carried out, on the reduction of unwanted 7-N acylated cephalosporin compounds. $H_2SO_4$ was used as acid.

TABLE 2d

Results of experiment 2 (30 liters of resin in an SMB-system was applied)

| | Feed | | | | Eluate | | | | Reduction (−) | | |
|---|---|---|---|---|---|---|---|---|---|---|---|
| | comp 1 | comp 2 | comp 3 | comp 4 | comp 1 | comp 2 | comp 3 | comp 4 | | | |
| Exp | (kg) | (kg) | (kg) | (kg) | (kg) | (kg) | (kg) | (kg) | comp 2 | comp 3 | comp 4 |
| 2K | 1.46 | 0.08 | 0.20 | 0.15 | 1.38 | 0.01 | 0.01 | 0.02 | 7 | 18 | 7 | comp 1: dipyl-7-ADCA
comp 2: alpha-hydroxyadipyl-7-ADCA
comp 3: alpha-aminoadipyl-7-ADCA
comp 4: adipic acid This example illustrates the use of adsorption chromatography performed according to the so-called Simulated Moving Bed technique, on a kilogram scale. The technique may readily be scaled up further.

The so treated fractions 2A to 2K were treated with acylase to produce 7-ADCA as described in Example 1. Excellent conversion results were obtained, as illustrated in Example 3.

EXAMPLE 3

Enzymatic Conversion

This example illustrates the results of enzymatic conversion of adipyl-7-ADCA to 7-ADCA. The adipyl-7-ADCA was recovered as disclosed in Example 2K (pH-treatment according to Example 1A, adsorption chromatography was optimised in terms of overloading and washing). The conversion was carried out as described in Example 1, at the pH indicated in Table 3. Experiment A to E represent different batches.

TABLE 3

| Exp | substrate comp 1 (mmol) | Substrate comp 2 (mmol) | pH (−) | Product stream comp 1 (mmol) | product stream comp 2 (mmol) |
|---|---|---|---|---|---|
| A | 69.7 | 2.2 | 8.5 | 1.1 | 68.6 |
| B | 144.2 | 2.4 | 8.5 | 5.9 | 143.3 |
| C | 181.4 | 2.3 | 8.5 | 13.5 | 174.5 |
| D | 113.1 | 1.7 | 8 | 5.4 | 108.7 |
| E | 113.4 | 3.1 | 9 | 1.2 | 112.2 | comp 1: adipyl-7-ADCA
comp 2: 7-ADCA

The conversion rate and yields are superior when the adipyl-7-ADCA is pre-treated using the pH/temperature step, as compared to no treatment. The further purification using chromatography brings further improvement in terms of purity (not shown in the Table).

EXAMPLE 4

Crude Crystallisation

The broth is pH/heat-treated (Example 1) and enriched in adipyl-7-ADCA by adsorption chromatography as described in Example 2. Subsequently, conversion was carried out as described in Example 1.

The conversion solution (the solution obtained after deacylation) was concentrated with reversed osmosis to increase the concentration.

Part of the solution was taken and the 7-ADCA was crystallised by lowering the pH to the pH 3.6, 4 or 5 (see table 4a).

TABLE 4a

Crude crystallisation

| Exp | comp 1 in solution | pH (−) | product after isolation, washing and drying (g) | comp 1 in product (%) |
|---|---|---|---|---|
| A | 49.5 | 3.6 | 48.9 | 97.5 |
| B | 49.5 | 4 | 48.7 | 97.4 |
| C | 49.5 | 5 | 48.2 | 98 | comp 1: 7-ADCA

Crystallisation was satisfactory at all pH tested. In the following experiment the pH was 3.6. The effect of concentrating the solution is illustrated.

TABLE 4b

Crude crystallisation

| Exp | comp 1 in solution (g) | product after isolation, washing and drying (g) | comp 1 in product (%) |
|---|---|---|---|
| D | 15.5 | 14.8 | 94.3 |
| E | 36.1 | 35.7 | 95.3 |
| F | 49.5 | 48.9 | 97.5 | comp 1: 7-ADCA

Clearly, there is an effect of the concentration of 7-ADCA in the conversion solution on purity and yield after crystallisation.

The following example illustrates the effect of different adsorbers on product quality (colour in solution and clarity).

TABLE 4c

Crude crystallisation

| Exp | comp 1 in solution (g) | treatment | comp 1 in product (%) | colour in solution at 425 nm (−) | clarity in HCl (EBC) |
|---|---|---|---|---|---|
| G | 25 | HP20 | 97.2 | 0.16 | 3.6 |
| H | 25 | HP20 (2 times) | 97.8 | 0.11 | 2.4 |
| I | 25 | IRA67 | 97.2 | 0.18 | 6 |
| J | 25 | IRA67 + HP20 | 97.7 | 0.1 | 0.8 |
| K | 25 | none | 96.3 | 0.39 | 7.3 | comp 1: 7-ADCA

EXAMPLE 5

Treatment of Dissolved 7-Amino Desacetoxy Cephalosporanic Acid

This example shows the effect on clarity and colour of 7-ADCA, after treating 7-ADCA solution with different adsorber resins, prior to crystallisation.
A solution comprising 7-ADCA is made as disclosed in Example 2K (the adsorption chromatography column used is a XAD-1600 resin).

TABLE 5

| Exp | comp 1 dissolved (g) | treatment | Colour in solution at 425 nm (−) | Clarity in HCl (EBC) |
|---|---|---|---|---|
| A | 40 | — | 0.18 | 4.2 |
| B | 40 | XAD16 | 0.05 | 1.8 |
| C | 40 | HP20 | n.d. | 0.5 |
| D | 40 | XAD1600 | 0.09 | 0.5 |
| E | 25 |  | n.d. | 3.6 |
| F | 25 | +1% EtOH | 0.11 | 0.6 |
| G | 50 | +3% EtOH | 0.18 | 0.9 |
| H | 50 | +2% Coal | 0.04 | n.d. |
| I | 50 |  | 0.17 | 1.4 |
| J | 50 | +5% Coal | 0.03 | 0.8 | comp 1: 7-amino desacetoxy cephalosporanic acid

EXAMPLE 6

Recovery of Adipyl-7-ADCA Using Extraction with N-Butanol

Broth comprising adipyl-7-ADCA is treated as described in Example 1.

After acidification, part of the adipyl-ADCA is purified by adsorption chromatography. The solution is pumped over a column filled with XAD-16 resin, washed with water, and eluted with 0.2 M acetate-solution. The first eluate fraction with low adipyl desacetoxy cephalosporanic acid content is taken out and discarded. The second fraction is collected. The resin is purified by washing with caustic and acetone, and conditioned again with acidified water.

Part of the adipyl-7-ADCA is purified by means of extraction, followed by washing of the extract, back extraction of the N-substituted cephalosporin from the organic phase to an aqueous phase and stripping the aqueous phase; the extracting organic solvent is n-butanol.

The adipyl-7-ADCA is treated with immobilised acylase to produce 7-amino desacetoxy cephalosporanic acid (7-ADCA). Part of the 7-ADCA is isolated by lowering the pH. The adipyl desacetoxy cephalosporanic acid was dissolved with the aid of caustic. The 7-amino desacetoxy cephalosporanic acid was isolated by lowering the pH.

Part of the 7-amino desacetoxy cephalosporanic acid aqueous solution is acidified, and the side chain is extracted to an extracting organic solvent and next the phases are separated; the extracting organic solvent was n-butanol, Finally the crystal cake was filtrated, washed and dried.

TABLE 6

| Exp | description | comp 1 in product (%) | colour 1 in solution at 425 nm (−) | clarity in HCl (EBC) |
|---|---|---|---|---|
| A | extraction/extraction/crystallisation | 98.3 | 0.13 | 2.4 |
| B | chromatography/extraction/crystallisation | 98.9 | 0.09 | 1.5 |
| C | chromatography/crystallisation | 97.6 | 0.12 | — |
| D | chromatography/crystallisation/recrystallisation | 98.7 | 0.05 | 1.1 |

Comp 1: 7-amino desacetoxy cephalosporanic acid

The results using a single extraction are not shown in the table, but the purity is far worse than when chromatography is used, even without recrystallisation. A combination of chromatography and recrystallisation produces or a combination of chromatography and extraction produces the best results.

EXAMPLE 7

Recovery of Adipic Acid from 7-ADCA Crystallisation Mother Liquors

7-ADCA crystallisation mother liquors are obtained as described in example 4. Adipic acid is determined using HPLC: Aminex HPX-87H column, 300 mm×7.8 mm, filled with 9 um cation gel (Biorad), eluted at 65° C. with a 0.2M solution of $H_2SO_4$ in water, detection using an RI Waters 410 refractometer. In the examples given below, optimisation is directed at purity, not at yield.

EXAMPLE 7A

Recovery of Adipic Acid Using Acidification

At 20° C., the pH of 7-ADCA crystallisation mother liquor (250 ml, 13.6 g/l adipic acid) was lowered to 0.7 using a 12M solution of $H_2SO_4$ in water. After 16 h at 0° C., no crystallisation could be detected. The pH was raised to 3.4 using a 6M solution of KOH in water. The resulting crystal was recovered by filtration to give 7.7 g of material which was a mixture of salt and adipic acid which was not further analysed.

EXAMPLE 7B

Recovery of Adipic Acid Using Acidification and Concentration

At 20° C., the pH of 7-ADCA crystallisation mother liquor (500 ml, 9.4 g/l adipic acid) was lowered to 1.5 using a 12M solution of $H_2SO_4$ in water and concentrated under reduced pressure at 40° C. to give a sticky mixture that was isolated by filtration and dried to give 6.9 g adipic acid with a purity of 53% (yield 78%).

EXAMPLE 7C

Recovery of Adipic Acid Using Reverse Osmosis with Nanomax 50 Membrane

At 20° C., the pH of 7-ADCA crystallisation mother liquor (500 ml, 9.4 to 18.2 g/l adipic acid, see table) was adjusted to the value mentioned in the table using either a 6M solution of KOH in water or a 12M solution of $H_2SO_4$ in water. The resulting solution was subjected to reverse osmosis using a Nanomax 50 membrane from Millipore. With the aid of nitrogen gas, a pressure of 30 bar was applied to give a filtrate and a retentate in which the amount of adipic acid was determined using HPLC. In most cases, a work-up procedure was applied that consisted of concentration under reduced pressure until crystallisation began, followed filtration of the product and drying.

TABLE 7

| | Adipic acid (g/l) | | | Retention (%) | Volume permeate (ml) | Yield after work-up (g) | Purity after work-up (%) |
|---|---|---|---|---|---|---|---|
| pH | Start | Permeate | Retentate | | | | |
| 1.5 | 13.6 | 11.0 | 14.8 | 26 | 400 | 4.4 | 96 |
| 2.0 | 18.2 | 13.1 | 20.8 | 37 | 260 | 2.4 | 99 |
| 3.0 | 9.4 | 6.7 | 8.7 | 23 | 360 | 1.9 | 97 |
| 7.2 | 13.6 | 5.3 | 31.9 | 83 | 400 | no work-up | no work-up |

EXAMPLE 7D

Recovery of Adipic Acid Using Reverse Osmosis with DK U19F Membrane at pH 2.0

The pH of 7-ADCA crystallisation mother liquor (100 l, containing 25.0 g/l adipic acid) was lowered to 2.0 using 2.9 l of a 12M solution of $H_2SO_4$ in water. The resulting solution was subjected to reverse osmosis with 57 l water using a DK U19F membrane in a 2.5 $m^2$ membrane filtration unit P2-B200 from Hydro Air Research. At a pressure of 30 bar an average flux of 8.8 $l/m^2/h$ was reached to give the results summarised in the table.

TABLE 8

| | Concentration (g/l) | | | Retention (%) |
|---|---|---|---|---|
| Component | Start | Permeate | Retentate | |
| Adipic acid | 25.0 | 11.6 | 17.8 | 35 |
| 7-ADCA | 0.72 | <0.01 | 0.72 | >99 |
| Adipyl-7-ADCA | 1.51 | <0.03 | 1.54 | >98 |

What is claimed is:

1. A process for the recovery from a complex mixture of a compound of formula (I):

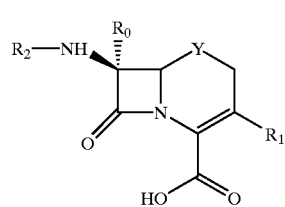

(I)

wherein $R_0$ is hydrogen or $C_{1-3}$ alkoxy;

Y is $CH_2$, oxygen, sulphur, or an oxidised form of sulphur;

$R_1$ is selected from the group consisting of hydrogen;

hydroxy;

halogen;

saturated or unsaturated, straight or branched alkyl (1–5 carbon atoms), optionally substituted with hydroxy, halogen, aryl, or alkoxy (1–3 carbon atoms) or acyl;

alkoxy (1–3 carbon atoms), optionally substituted with hydroxy or halogen;

cycloalkyl (3–8 carbon atoms) optionally substituted with hydroxy, halogen, or amino;

aryl; and heteroaryl;

$R_2$ is selected from the group consisting of adipyl, succinyl, glutaryl, pimelyl, suberyl, 2-(carboxyethylthio)acetyl, 3-(carboxyethylthio) propionyl, higher alkyl saturated and higher alkyl unsaturated dicarboxylic acids, wherein said complex mixture comprises in addition to the compound of formula (I), 6-aminopenicillanic acid (6-APA) and optionally one or more additional N-substituted β-lactam compounds, comprising the steps of:

(a) acidifying the complex mixture to a pH below 6.5 and maintaining the mixture below said pH at a temperature of between 50° C. and 130° C.; and/or (b) contacting the complex mixture with a carbon dioxide source; and (c) subjecting the mixture obtained after steps (a) and/or (b) to adsorption chromatography to obtain the compound of formula (I).

2. The process of claim 1, wherein in step (a) the temperature is kept between 70 and 120° C., for between 10 seconds and about 1 day and the pH is kept at or below pH 4.5.

3. The process of claim 1, wherein the compound of formula (I) has been produced by fermentation of a microorganism capable thereof and wherein the complex mixture is a broth, a culture filtrate or any culture liquid derivable from the broth after fermentation.

4. The process of claim 1, wherein the compound of formula (I) is selected from the group consisting of adipyl-7-amino desacetoxy cephalosporanic acid (adipyl-7-ADCA), adipyl-7-amino desacetyl cephalosporanic acid (adipyl-7-ADAC) and adipyl-7-amino cephalosporanic acid (adipyl-7-ACA).

5. The process of claim 1, wherein said chromatography is hydrophobic interaction chromatography.

6. The process of claim 1, which further comprises deacylating the compound of formula (I) to obtain a conversion solution which comprises a compound of formula (II)

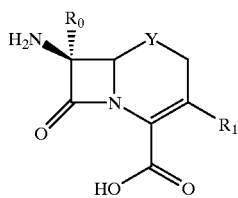

(II)

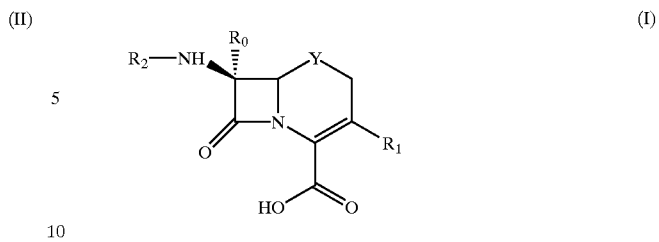

(I)

wherein $R_0$ is hydrogen or $C_{1-3}$ alkoxy,

Y is $CH_2$, oxygen, sulphur, or an oxidised form of sulphur;

$R_1$ is selected from the group consisting of
- hydrogen;
- hydroxy;
- halogen;
- saturated or unsaturated, straight or branched alkyl (1–5 carbon atoms), optionally substituted with hydroxy, halogen, aryl, or alkoxy (1–3 carbon atoms) or acyl;
- alkoxy(1–3 carbon atoms), optionally substituted with hydroxy or halogen;
- cycloalkyl (3–8 carbon atoms) optionally substituted with hydroxy, halogen, or amino;
- aryl;
- heteroaryl;

$R_2$ is selected from the group consisting of adipyl, succinyl, glutaryl, pimelyl, suberyl, 2-(carboxyethylthio)acetyl, 3-(carboxyethylthio)propionyl, higher alkyl saturated and higher alkyl unsaturated dicarboxylic acids, wherein said complex mixture comprises in addition to the compound of formula (I), 6-aminopenicillanic acid (6-APA) and optionally one or more additional N-substituted β-lactam compounds, comprising the steps of:

(a) acidifying the complex mixture to a pH below 6.5 and maintaining the mixture below said pH at a temperature of between 50° C. and 130° C.; or (b) contacting the complex mixture with a carbon dioxide source; but not both (a) and (b), and (c) subjecting the mixture obtained after steps (a) or (b) to adsorption chromatography to obtain the compound of formula (I).

wherein $R_0$, $R_1$ and Y are as defined in claim 1 and the cleaved side chain $R_2OH$.

7. The process of claim 6, wherein the deacylating comprises treating the compound of formula (I) with a dicarboxylate acylase.

8. The process of claim 6, comprising the further step of recovering the compound of formula (II) from the solution by crystallisation.

9. The process of claim 8, wherein crystallisation is preceded by treating the solution with an agent selected from the group consisting of an adsorber resin, active coal, methanol, ethanol, isopropanol, isobutanol, n-butanol, acetone or a combination of any of the mentioned agents.

10. The process of claim 9, wherein the agent includes at least an adsorber resin selected from AMBERLITE® XAD16, AMBERLITE® XAD1600 and Diaion™ HP20.

11. The process of claim 6, wherein the 6-aminopenicillanic acid (6-APA) level is 10 ppm or less.

12. The process of claim 8, which comprises the further step of removing at least partially, the cleaved side chain $R_2OH$.

13. The process of claim 12, wherein said removing is carried out on the mother liquor obtained after crystallisation.

14. The process of claim 13, wherein said removing is followed by solubilizing of the crude crystals and recrystallizing the compound of formula (II).

15. The process of claim 13, wherein crystallisation is preceded by treating the solution with an agent selected from the group consisting of an adsorber resin, active coal, methanol, ethanol, isopropanol, isobutanol, n-butanol and acetone, or a combination of any of these mentioned agents.

16. process of claim 12, wherein said removing comprises subjecting the conversion solution, or the mother liquor, to membrane filtration at a pH below 5.

17. A process for the recovery from a complex mixture of a compound of formula (I):

* * * * *